United States Patent [19]

Hess et al.

[11] Patent Number: 5,545,210
[45] Date of Patent: Aug. 13, 1996

[54] METHOD OF IMPLANTING A PERMANENT SHAPE MEMORY ALLOY STENT

[75] Inventors: Robert L. Hess, Portola Valley; John E. Bramfitt, Woodside, both of Calif.

[73] Assignee: Advanced Coronary Technology, Inc., Menlo Park, Calif.

[21] Appl. No.: 310,100

[22] Filed: Sep. 22, 1994

[51] Int. Cl.⁶ ........................................................ A61F 2/06
[52] U.S. Cl. .................................. 623/1; 623/11; 623/12; 606/198
[58] Field of Search ............................... 606/191, 194, 606/195, 198; 623/1, 12; 604/281

[56] References Cited

U.S. PATENT DOCUMENTS

| | | | |
|---|---|---|---|
| 3,657,744 | 4/1972 | Ersek | 623/11 |
| 3,868,956 | 3/1975 | Alfidi et al. | 606/194 |
| 4,170,990 | 10/1979 | Baumgart et al. | 606/78 |
| 4,503,569 | 3/1985 | Dotter | 623/1 |
| 4,512,338 | 4/1985 | Balko et al. | 606/108 |
| 4,553,545 | 11/1985 | Maass et al. | 606/198 |
| 4,580,568 | 4/1986 | Glanturco | 606/198 |
| 4,655,771 | 4/1987 | Wallsten | 623/1 |
| 4,665,906 | 5/1987 | Jervis | 606/78 |
| 4,665,918 | 5/1987 | Garza et al. | 606/108 |
| 4,733,665 | 3/1988 | Palmaz | 606/108 |
| 4,739,762 | 4/1988 | Palmaz | 606/108 |
| 4,759,906 | 7/1988 | Nenno et al. | 420/463 |
| 4,762,128 | 8/1988 | Rosenbluth | 606/192 |
| 4,776,337 | 10/1988 | Palmaz | 606/108 |
| 4,795,458 | 1/1989 | Regan | 623/1 |
| 4,856,516 | 8/1989 | Hillstead | 606/194 |
| 4,865,663 | 9/1989 | Tuominen et al. | 148/402 |
| 4,886,062 | 12/1989 | Wiktor | 606/194 |
| 4,893,623 | 1/1990 | Rosenbluth | 606/192 |

(List continued on next page.)

FOREIGN PATENT DOCUMENTS

| | | |
|---|---|---|
| 0119688 | 9/1984 | European Pat. Off. . |
| 0364787A1 | 4/1990 | European Pat. Off. . |
| 0380666 | 8/1990 | European Pat. Off. . |
| 0380666A1 | 8/1990 | European Pat. Off. . |
| 0606165A1 | 7/1994 | European Pat. Off. . |
| 57-89859 | 6/1982 | Japan . |
| 57-176154 | 10/1982 | Japan . |
| 58-501458 | 9/1983 | Japan . |
| 60-220030 | 11/1985 | Japan . |
| 61-220648 | 9/1986 | Japan . |
| 62-82975 | 4/1987 | Japan . |
| 62-82976 | 4/1987 | Japan . |
| 2135585 | 4/1982 | United Kingdom . |
| 83-00997 | 3/1983 | WIPO . |
| 8801029 | 10/1988 | WIPO . |
| 89-02755 | 4/1989 | WIPO . |
| 8800960 | 3/1990 | WIPO . |
| WO92/19310 | 11/1992 | WIPO . |
| WO93/08767 | 5/1993 | WIPO . |
| WO94/20044 | 9/1994 | WIPO . |

OTHER PUBLICATIONS

Dotter et al., "Transluminal Expandable Nitinol Coil Stent Grafting: Preliminary Report", Apr. 1983, Radiology, vol. 147, pp. 259–260.

Cragg et al., "Nonsurgical Placement of Arterial Endoprostheses: A New Technique Using Nitinol Wire", Apr. 1983, Radiology, vol. 147, pp. 261–263.

Wright et al., "Percutaneous Endovascular Stents: An Experimental Evaluation", 1985, Radiology, vol. 156, pp. 69–72.

Scherky McDonald, "Shape–Memory Alloys", pp. 74–82.

*Primary Examiner*—Gary Jackson
*Assistant Examiner*—Patrick W. Rasche
*Attorney, Agent, or Firm*—Burns, Doane, Swecker & Mathis, L.L.P.

[57] ABSTRACT

A permanent tissue supporting device, and a method for supporting tissue, wherein a stent-like member comprising a shape-memory alloy is permanently positioned to support the tissue of a tubular organ of a living body. The shape-memory alloy of the positioned stent-like member is in the martensitic state and exhibits a strain on a horizontal plateau of a stress-strain curve of the shape-memory alloy when permanently positioned in the tubular organ.

7 Claims, 1 Drawing Sheet

U.S. PATENT DOCUMENTS

| | | | |
|---|---|---|---|
| 4,913,141 | 4/1990 | Hillstead | 606/108 |
| 4,954,126 | 9/1990 | Wallsten | 600/36 |
| 4,969,458 | 11/1990 | Wiktor | 606/194 |
| 4,969,890 | 11/1990 | Sugita et al. | 606/192 |
| 5,037,427 | 8/1991 | Harada et al. | 606/108 |
| 5,071,407 | 12/1991 | Termin et al. | 604/104 |
| 5,089,005 | 2/1992 | Harada | 606/194 |
| 5,104,404 | 4/1992 | Wolff | 623/1 |
| 5,114,504 | 5/1992 | AbuJudom, II et al. | 148/402 |
| 5,195,984 | 3/1993 | Schatz | 606/195 |
| 5,197,978 | 3/1993 | Hess | 623/1 |
| 5,201,901 | 4/1993 | Harada et al. | 606/198 |
| 5,219,358 | 6/1993 | Bendel et al. | 606/222 |
| 5,242,451 | 9/1993 | Harada et al. | 606/108 |

METHOD OF IMPLANTING A PERMANENT SHAPE MEMORY ALLOY STENT

FIELD OF THE INVENTION

The invention relates to tissue supporting devices (stents), preferably vascular stents for reputing blood vessels, and more particularly, to non-removable devices which will permanently support a dilated stenosis of a tubular organ (hollow viscus) such as a blood vessel.

BACKGROUND OF THE INVENTION

In the past, permanent or biodegradable devices have been developed for implantation within a body passageway to maintain vascular patency. These devices are typically characterized by the ability of such an intravascular device to be enlarged radially after having been introduced percutaneously, to be transported transluminally, and to be positioned in a desired location. These devices are either expanded mechanically, such as by the expansion of a mandrel positioned inside the device, or are capable of releasing stored energy to expand themselves upon actuation within the body.

U.S. Pat. Nos. 4,739,762, 4,776,337 and 4,733,665 disclose expandable and deformable intraluminal vascular grafts in the form of thin-walled tubular members which are expanded radially outwardly into contact with a body passageway, the members being plastically deformed beyond their elastic limit and the members being permanently fixed within the body. Suitable materials for the fabrication of these tubular-shaped members would include silver, tantalum, stainless steel, gold, titanium, or other suitable plastically deformable materials which may be permanently deformed. Permanent deformation is achieved when the material is subjected to a force which creates a strain greater than the elastic limit of the material which is utilized to make the tubular member. The open-mesh configuration of such devices is soon encapsulated by body tissue and cannot be removed. The exceeding of the elastic limit of the material used in such devices is also believed to compromise the performance of the devices in situ.

U.S. Pat. No. 4,969,458 discloses a vascular stent formed from a wire component made of material, such as copper alloy, titanium, or gold, wherein the wound configuration unwinds upon expansion and becomes a permanent prosthesis stent, similar to prior art devices disclosed above, and is not removable.

U.S. Pat. No. 4,969,890 discloses various configurations of shape-memory alloy members which have been previously radially compressed and which, upon positioning within the body and thermal activation, expand by themselves to become a permanent prosthesis within the body. In this regard, the reference teaches a device which operates in a similar fashion to the device disclosed in U.S. Pat. No. 4,485,816. U.S. Pat. No. 4,485,816 discloses a shape-memory alloy staple which, when heated, penetrates and cinches tissue together. Shape-memory alloy historically has been used to perform work in such a fashion wherein the component remains in a strong austenitic state after temperature activation. That is, above its transition temperature from marten site to austenite, and as the references above disclose, the shape-memory alloy either dilates an incompetent blood vessel or holds segments of tissue together. Neither of these devices is practically removable by a method which does not require surgery.

Shape-memory alloys possess the useful characteristic of being capable of changing physical dimensions upon heating above a first transition temperature, $A_f$, between a soft martensitic metallurgical state and a hard austenitic metallurgical state of the alloys. A shape-memory alloy member can be processed while in a high temperature austenitic phase to take on a first configuration. After cooling the shape-memory alloy member below a second transition temperature $M_f$ between the austenitic and martensitic states without change of physical dimensions, the shape-memory alloy member can be mechanically deformed into a second configuration. The shape-memory alloy member will remain in this second configuration until further heating to a temperature above $A_f$ at which time the shape-memory alloy member will revert to its first configuration. A shape-memory alloy member can exert large forces on adjacent members during the transition from the second configuration to the first configuration. Numerous inventions have taken advantage of shape-memory alloy members capable of exerting this thermally activated force.

Shape-memory alloys have the further useful characteristic that, in the martensitic phase, the stress-strain curve exhibits a plateau indicating that a limited increase in strain can be achieved with imperceptible increase in stress. This martensitic stress-strain plateau usually defines the range of mechanical strain which can be recovered by the application of heat. Exceeding the upper end of this strain range may result in non-heat recoverable deformation.

U.S. Pat. No. 5,197,978, hereby incorporated by reference, discloses shape-memory alloy tissue supporting devices that are made to expand or shrink radially upon mechanical or thermal actuation, and, in particular, devices that are removable from the body.

It would be advantageous to have a tissue supporting device of a generally tubular configuration which can be inserted into a body duct or cavity while in an unexpanded shape and then be expanded to provide permanent support for the tissue forming the duct or cavity, such that the device when expanded does not exert a radial load on the supported duct or cavity and where the device when expanded has sufficient crush resistance to provide support for the duct or cavity when the duct or cavity exerts a normal radial compressive load on the device as the result of major contractions of the tissue.

It would be further advantageous to have a tissue supporting device, for simultaneous support of cavities of different sizes, in which larger expanded device sizes do not require higher expansion pressures than smaller device sizes, so that the potential for dissection and/or tissue damage is minimized, and where further the device remains somewhat flexible to accommodate movement of soft tissue.

It would be further advantageous to have a heat-to-expand tissue supporting device that does not need to be cooled prior to installation and which provides permanent tissue support while in the martensite state during service.

It would be further advantageous to have a method for reversibly manipulating the configuration of a device designed for tissue support, in order to facilitate machining, deburring, etc. of hard-to-reach interior surfaces of the device without affecting the functionality of the device in a final product.

SUMMARY OF THE INVENTION

The invention provides a tissue supporting device comprising a stent-like member of a shape-memory alloy which transforms from a martensitic metallurgical state to an austenitic metallurgical state when heated above a first transition temperature $A_f$ and transforms from the austenitic state to the martensitic state when cooled below a second transition temperature $M_f$. The stent-like member is mechanically deformable without plastic deformation in a body passage of a living person from a first configuration while in the martensitic state to a second configuration in the martensitic state and the $A_f$ and $M_f$ transition temperatures are sufficiently above a body temperature of the living person to prevent recovery of the stent-like member to the first configuration by heating the stent-like member above $A_f$ without permanently damaging surrounding tissue of the living person, the stent-like member exhibiting a strain on a horizontal plateau of a stress-strain curve of the shape-memory alloy when permanently positioned in the tubular organ.

The stent-like member can have various features. For instance, the stent-like member can have a tubular shape with a plurality of slots, each of the slots extending parallel to a central axis of the stent-like member. The slots can be rectangular in shape and ends of the slots circumferentially adjacent to each other can be offset in an axial direction. The slots can form a uniform pattern with at least two axially spaced-apart slots aligned with each other at locations spaced circumferentially around the stent-like member. In the expanded condition, the stent like member can have an essentially cylindrical, mesh-like shape which inhibits thrombosis when expanded in an artery of a living person. The stent-like member can include struts and the stent-like member can be radially expanded to an expanded configuration wherein the stent-like member has a planar cylindrical profile and the struts are not twisted such that edges thereof project radially outwardly. The shape-memory alloy is preferably an alloy of Ni and Ti having an $A_f \geq 62°$ C. The stent-like member can includes at least one hinge-like member extending between adjacent sections of the stent-like member. The hinge-like member can be formed integral with the sections of the stent-like member and the hinge-like member can have an axial length shorter than an axial length of each section of the stent-like member. The hinge-like member can comprises a single axially extending strip of the shape-memory alloy.

The invention also provides a method of implanting a tissue supporting device comprising a stent-like member of a shape-memory alloy having martensitic and austenitic metallurgical states and a transition temperature $A_f$ therebetween. The method includes mechanically expanding the stent-like member in its martensitic state followed by heating the expanded stent-like member above $A_f$ and further expanding the stent-like member after which the stent-like member is cooled to body temperature. The $A_f$ temperature can be above 37° C. and below 62° C., for instance 40° to 50° C. and the alloy can be a NiTi alloy. The method can further include crimping the tissue supporting device onto a balloon located at a distal end of a catheter and navigating the tissue supporting device to an application site within the tubular organ. The expanding step can be carried out by mechanically expanding the tissue supporting device until the balloon is fully inflated.

DETAILED DESCRIPTION OF THE INVENTION

According to the invention, a tissue supporting device is provided which can be inserted into a body passage, such as a blood vessel, duct or cavity, and used to support the tissue forming the duct or cavity. In particular, a tissue supporting device comprising a material which exhibits a stress-strain curve wherein an increase in strain can be achieved with a negligible increase in stress. The tissue supporting device is of generally tubular shape is provided which can be inserted into a body duct or cavity in an unexpanded shape and then be expanded at a desired position in the duct or cavity to form a permanent supporting structure for the tissue surrounding the expanded device.

The tissue supporting device can be fabricated from a shape memory alloy such as a binary Ni-Ti alloy or NiTi alloy having one or more additional elements added thereto. Other possibilities include shape memory alloys from the Cu-Al-Ni system. Such alloys have martensitic and austenitic metallurgical states and a transition temperature therebetween. The shape-memory alloy according to the invention is characterized by a stress/strain curve in the martensite state wherein a limited increase in strain can be achieved with imperceptible increase in stress.

A tissue supporting device according to the invention can be made from a Ni-Ti alloy whose tensile strength in the martensitic state at human body temperature is 8 to 25 ksi. According to one embodiment of the invention, the transition temperature at which the alloy transforms from the martensitic to the austenitic state is preferably at a temperature of 70° C. or higher. At such temperatures, known thermal recovery techniques for shrinking shape memory alloy tubular devices can not be used to recover the tissue supporting device without causing permanent damage to surrounding tissue or blood due to thermal trauma which has been found to occur when tissue/blood is exposed to temperatures above 62° C.

Figure 1:
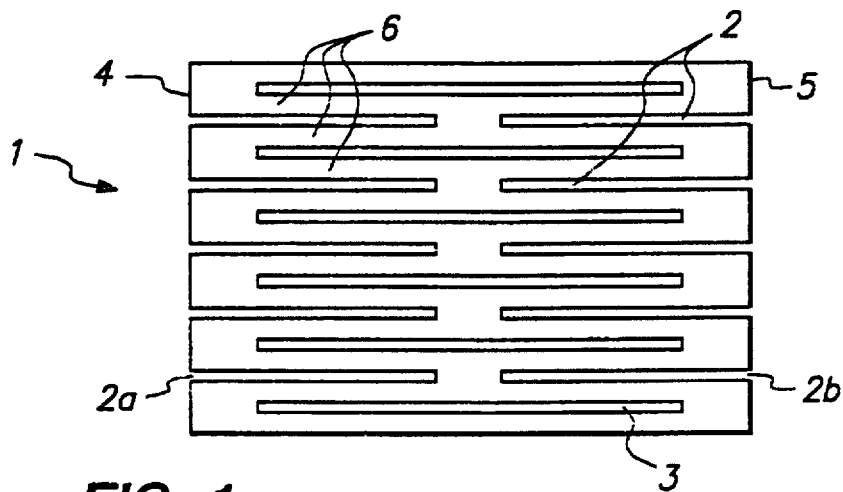
FIG. 1 shows a side view of a tissue supporting device in accordance with the invention.
Figure 2:
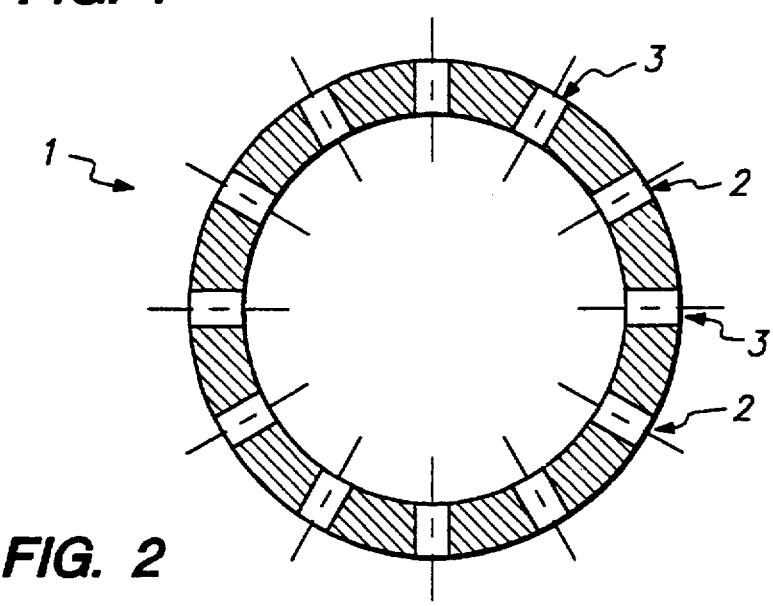
FIG. 2 shows a cross-sectional view of a tissue supporting device in accordance with the invention.

A first embodiment of a tissue supporting device 1 in accordance with the invention is shown in FIGS. 1 and 2. As shown in the side view of FIG. 1, the device 1 includes a plurality of rectilinear slots 2, 3. Slots 2 are arranged in axially aligned pairs such that a first slot 2a intersects one axial end 4 of the device 1 and the other slot 2b intersects the other axial end 5 of the device 1. Slots 3 are arranged such that circumferentially adjacent slots 3 are separated by a pair of the aligned slots 2. Further, a single slot 3 is located between axial ends 4, 5. As shown in FIG. 2, slots 2, 3 are distributed in a uniform pattern around the devices. When the device 1 is expanded by inflating a balloon of a balloon catheter, legs 6 extending between axial ends of slots 2, 3 are mechanically deformed such that they are no longer parallel to the center axis of device 1.

Figure 3:
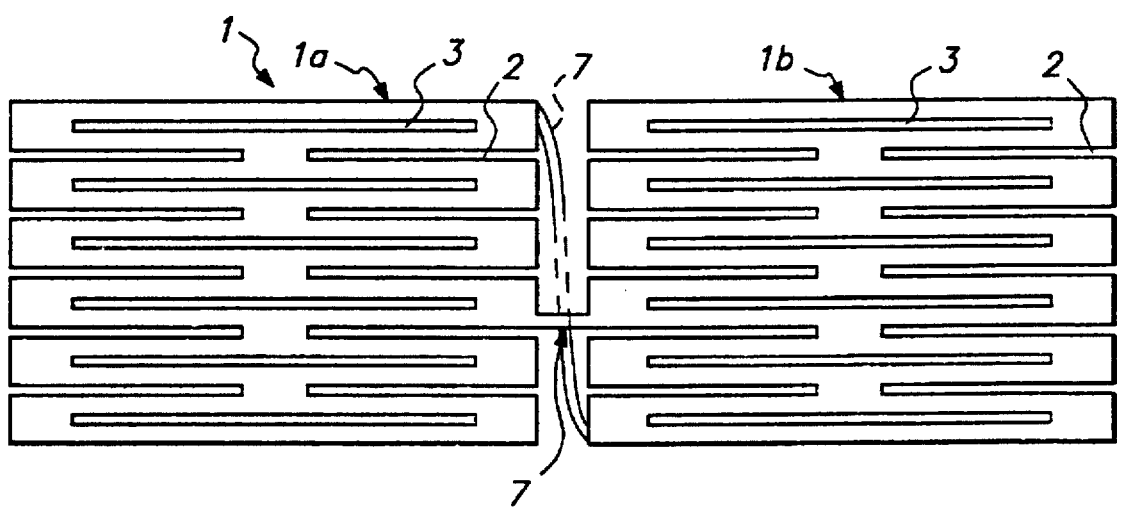
FIG. 3 shows a tissue supporting device in accordance with the invention comprising two tissue supporting elements joined by a bridging system.

FIG. 3 shows a device 1 comprising first and second sections 1a, 1b joined by bridging member 7. The bridging member can have any suitable configuration such as a straight, helical (shown in phantom in FIG. 3) curved or wavy strip. If desired, any number of sections of device 1 could be interconnected by bridging members 7. Also, adjacent sections of device 1 can be connected by a plurality of bridging members which are spaced apart and distributed at different locations around the circumference of the stent.

The arrangement shown in FIG. 3 is advantageous for negotiating tortuous body cavities such as blood vessels having sharply angled bends therein and for expanding sections 1a, 1b to different diameters.

The stent-like member 1 according to the claimed invention, when fabricated from a Ni-Ti shape-memory alloy, can be expanded in a blood vessel to a range of desired sizes by inflating a balloon catheter to a pressure of 4–10, preferably 6–8 atmospheres of pressure in the balloon catheter. When the stent is expanded, the slots are enlarged into generally diamond shaped rectangular openings arranged in a uniform pattern that is in the form of a mesh-like lattice. In the embodiment shown in FIG. 3, expansion of the individual stent-like members 1a, 1b can be performed separately to achieve different diameters. Due to the expansion in the martensitic condition, stent-like members expanded to larger sizes do not require higher expansion pressures than stent-like members expanded to smaller sizes provided that the tissue supporting device comprises stent-like members made from the same generally tubular shape-memory alloy material. This embodiment offers the advantage of minimizing the potential for dissection and/or tissue damage.

The stent-like member 1 can be positioned at its application site in a low profile configuration with radial dimensions small enough to allow navigation of orifice and ducts leading to the site of application. The stent-like member 1 can be positioned by means of a balloon catheter device having a lumen portion, balloon portion, and guide portion with the stent-like member 1 surrounding the balloon portion. In a preferred embodiment, stent-like member 1 is mechanically crimped securely to the balloon portion prior to insertion of the balloon catheter device in a blood vessel.

In use, the balloon portion is expanded, thus deforming stent-like member 1 radially outward against an inner wall of a blood vessel, and forming a supporting structure for the blood vessel. The expansion of the stent-like member according to the invention takes place in the elastic region of the stress-strain curve defined by the horizontal plateau in that curve. The deformed stent-like member 1 can comprise the tubular shape shown in FIGS. 1–3 or any other suitable shape which can be mechanically deformed without permanently deforming the device. The stent is designed so that the strain in the expanded stent-like member 1 is controlled such as by slot length of the slots 2, 3. Use of a shape memory NiTi alloy for the device is advantageous since such material can exhibit anti-thrombotic properties.

Once the balloon catheter has been removed by collapsing the balloon portion, stent-like member 1 is left implanted to permanently support the blood vessel. The overall geometry of the stent-like member 1 ensures that the snapback at expansion is minimized and is proportional to the expanded size of the stent-like member 1. Since the implanted stent-like member exhibits a strain on a horizontal plateau on a stress-strain curve for the shape-memory alloy, the stent-like member can support the blood vessel at essentially constant stress. The expanded dimensions of the stent-like member 1 cannot be adjusted by the amount of force used to expand the device. Instead, the expanded diameter is controlled by the dimensions of the duct, cavity or, blood vessel, into which the stent-like member 1 is expanded. According to the invention, the shape memory alloy of the stent-like member 1 remains in the martensitic state when the stent-like member 1 is in service in a human body.

The duct supportive properties of an implanted member can be controlled by the wall thickness of shape-memory alloy forming the tube-like member, the length of longitudinal slots 2, 3 and by the degree of expansion of the stent-like member 1. An implanted stent-like member 1 has sufficient crush resistance to provide support for a duct or cavity or blood vessel when such duct or cavity or blood vessel exerts a normal radial compressive load on the stent-like member 1 as the result of a major contraction of the duct or cavity or blood vessel. Preferably the stent-like member 1 can be sufficiently robust to support a coronary artery when major contractions are indicated. The implanted stent-like member 1 essentially does not exert a radial load on the duct or cavity or blood vessel it is supporting. The implanted stent-like member 1 allows for a small amount of radial recoverable deflection at low loads as the supported duct or cavity or blood vessel contracts. The low force needed to cause elastically recoverable deflection of stent-like members 1 in response to tissue duct contraction can advantageously minimize irritation to the duct wall when small contractions occur.

Although the invention has been described as useful in an angioplasty procedure, it is understood that the invention is not limited to such a procedure or the use of a stent-like member in a blood vessel. It should be apparent to one skilled in the art that the invention is useful in supporting body tissue in general as well as various blood vessels, e.g., in saphenous vein grafts, the vena cavae, the aorta, the renal artery, the iliac artery, the femoral artery, the popliteal artery, the carotid artery, the cranial arteries, pulmonary arteries, etc. The various embodiments of the invention are also useful with other tubular organs including but not limited to the prostate, biliary tract, the esophagus, the trachea, the fallopian tubes, the vas deferens, the ureters, the tear ducts, the salivary ducts, etc.

According to another embodiment of the invention, a stent-like member is given a memory shape which is larger in size than the lumen of the body organ in which the stent is to be located. According to this embodiment, the stent-like member is conditioned by techniques known to those skilled in the art to memorize a large diameter and the shape memory alloy from which the stent is made has transformation temperatures $M_f$ and $A_f$ above body temperature. In use, the stent-like member is compressed in the martensitic condition to have a smaller diameter when the stent is put on a catheter. Then the stent-like member is introduced through a body organ by means of the catheter and once properly positioned, the stent is mechanically expanded by balloon expansion without plastic deformation of the stent, after which the stent is heated, in vivo, above body temperature to a transition temperature $A_f$ to expand the stent into the austenite condition and thus expand the stent-like member to the memorized larger diameter shape. Subsequently, the stent-like member is allowed to cool to body temperature and return to the martensitic condition. In a preferred embodiment, $A_f$ is above 37° C. and below 62° C. such as 40° to 50° C. and $M_f > 37°$ C.

The stent according to the second embodiment can be used in various ways. For instance, this heat expandable stent can be implanted by partial balloon expansion of the stent followed by complete expansion created by application of heat. The partial balloon expansion would be sufficient to locate the stent at the target site with final expansion aimed at producing a larger final diameter to support the artery. The heat activated final expansion would exert a radial force on the artery wall instantaneously as the stent takes on its austenitic phase when heated to an elevated temperature. This radial force embeds the stent in the artery wall in a controlled way as a result of interaction between the natural resilience of the arterial wall and predetermined final expanded diameter of the stent. After the stent is heat expanded, the blood stream rapidly cools the stent into its martensitic phase. As a result, the enhanced ductility of the martensitic phase allows the stent to accommodate variations in the diameter of the artery and provides a fixed stent diameter which does not exert a radial force on the artery, but rather simply acts as a support structure.

The heat expanded stent according to the second embodiment of the invention reduces the barotrauma associated with normal balloon implantation of stents by conventional balloon angioplasty. That is, it is well known that dissections of arterial walls can be caused by expanding balloons and internal trauma can be expected when any mechanical force is applied to the arterial walls. In the case of balloon angioplasty, the total balloon area contacts the inner arterial wall and the trauma is extensive. Furthermore, balloons can protrude through stent structures and extend beyond the ends of stents to give a similar effect. The heat expanded stent according to the second embodiment can avoid the barotrauma problem since it is not necessary to fully expand the stent by balloon expansion. That is, by partial expansion of the stent by using a balloon and final expansion by application of heat there is less contact of the inner arterial wall with foreign bodies such as the stent and balloon than in the case where a stent is fully expanded by balloon expansion. Thus, the heat expanded stent according to the second embodiment can be implanted in a manner which leaves the major area of the stented wall unaffected whereby lower levels of cell proliferation associated with recovery from the trauma and hence less restenosis will occur.

The tissue supporting device according to the claimed invention is non-magnetic and corrosion resistant. Further, the tissue supporting device can include means for making the stent visible and radiopaque under conventional fluoroscopes when in the human body. For instance, the radial wall thickness of the tissue supporting device can be from 0.005 inches to 0.020 inches, thus making the stent visible by radiopaque techniques.

In yet another embodiment of the invention, the stent-like member 1 with shape memory properties can be reversibly manipulated during its manufacture to facilitate secondary processes without affecting the functionality of the final stent-like member 1 product. For example, the original diameter of the stent-like member 1 may be increased to enable the internal surfaces to be mechanically altered by processes such as machining, deburring, etc., and later, the diameter of the stent-like member 1 can be returned to its original dimensions by heating the stent-like member 1 above the transition temperature of the shape memory alloy. By this method, stent-like members with interior surfaces of exceptional machined finish can be obtained in a final stent-like product. In addition, the stent can be surface treated and/or coated with any suitable material such as polymeric material found to be beneficial in providing a surface finish which minimizes thrombogenicity. If desired, the coating could also incorporate additives for drug delivery or other medical purposes.

The stent according to the invention can provide benefits in preventing thrombogenic response. In particular, the stent geometry can be controlled to provide a planar cylindrical profile when expanded with minimal strut twisting and outwardly protruding stent strut terminations. That is, whereas the struts forming the mesh-like structure of stainless steel stents have a tendency to twist such that the edges thereof project radially outwardly when expanded by balloon inflation, the stent according to the invention can be expanded without such twisting of the struts. Further, compared to a stainless steel stent having the same configuration, the stent according to the invention can be expanded at much lower balloon expansion pressures. The lower expansion pressures used in accordance with the invention minimize barotrauma and the smooth outer cylindrical surface of the expanded stent in accordance with the invention provides non-thrombogenic properties.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A method of implanting a permanent tissue supporting device comprising a stent-like member of a shape-memory alloy having martensitic and austenitic metallurgical states and a transition temperature $A_f$ therebetween, the method comprising sequential steps of (i) positioning the stent-like member in a tubular organ of a living body, (ii) mechanically expanding the stent-like member in its martensitic state to form a mechanically expanded shape, (iii) further expanding the stent-like member by heating the mechanically expanded shape above $A_f$ so that the stent-like member is transformed into the austenitic state and recovers a memorized configuration larger than the mechanically expanded shape, and (iv) cooling the stent-like member to body temperature.

2. The method according to claim 1, wherein $37° C. \leq A_f \leq 62° C.$

3. The method according to claim 1, wherein the mechanically expanding step expands the stent to a size smaller than the inner diameter of the tubular organ.

4. The method according to claim 1, wherein the stent-like member is positioned permanently to support tissue.

5. A method of supporting tissue, comprising the steps of:

positioning a permanent generally tubular tissue supporting device in a tubular organ of a living body, the tissue supporting device comprising a shape-memory alloy having martensitic and austenitic metallurgical states and a transition temperature of at least 70° C. therebetween; and permanently fixing the tissue supporting device in the tubular organ such that the tissue supporting device is in the martensitic state, the tissue supporting device exhibiting a strain on a plateau of a stress-strain curve of the shape-memory alloy when permanently positioned in the tubular organ.

6. The method according to claim 5, the positioning step comprising crimping the tissue supporting device onto a balloon located at a distal end of a catheter, and navigating the tissue supporting device to an application site within the tubular organ.

7. The method according to claim 6, the fixing step comprising mechanically expanding the tissue supporting device until the balloon is fully expanded.

* * * * *